US010722719B2

(12) United States Patent
Kim et al.

(10) Patent No.: US 10,722,719 B2
(45) Date of Patent: Jul. 28, 2020

(54) VIBRATION-BASED SECURE SIDE CHANNEL FOR MEDICAL DEVICES

(71) Applicants: THE TRUSTEES OF PRINCETON UNIVERSITY, Princeton, NJ (US); PURDUE RESEARCH FOUNDATION, West Lafayette, IN (US)

(72) Inventors: Younghyun Kim, West Lafayette, IN (US); Woo Suk Lee, Brownsburg, IN (US); Vijay Raghunathan, West Lafayette, IN (US); Niraj K. Jha, Princeton, NJ (US); Anand Raghunathan, West Lafayette, IN (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 47 days.

(21) Appl. No.: 15/552,180

(22) PCT Filed: Feb. 12, 2016

(86) PCT No.: PCT/US2016/017746
§ 371 (c)(1),
(2) Date: Aug. 18, 2017

(87) PCT Pub. No.: WO2016/133813
PCT Pub. Date: Aug. 25, 2016

(65) Prior Publication Data
US 2018/0043168 A1    Feb. 15, 2018

Related U.S. Application Data

(60) Provisional application No. 62/118,195, filed on Feb. 19, 2015, provisional application No. 62/132,778, filed on Mar. 13, 2015.

(51) Int. Cl.
*A61N 1/372* (2006.01)
*A61B 5/00* (2006.01)
(Continued)

(52) U.S. Cl.
CPC ........ *A61N 1/37217* (2013.01); *A61B 5/0028* (2013.01); *A61B 5/0031* (2013.01);
(Continued)

(58) Field of Classification Search
CPC ................................. A61N 1/37217
See application file for complete search history.

(56) References Cited

U.S. PATENT DOCUMENTS 5,304,206 A    4/1994  Baker, Jr. et al.
5,729,173 A *  3/1998  Sato ................... H04L 27/3872
                                                        329/308
(Continued)

FOREIGN PATENT DOCUMENTS

WO        01/10071 A1    2/2001

OTHER PUBLICATIONS

5axena, N. et al. "Treat 'Em Like Other Devices: User Authentication of Multiple Personal RFID Tags", in Symposium )n Usable Privacy and Security, poster session, Jul. 15-17, 2009.*
(Continued)

*Primary Examiner* — Alyssa M Alter
(74) *Attorney, Agent, or Firm* — Meagher Emanuel Laks Goldberg & Liao, LLP

(57) ABSTRACT

According to some embodiments, a system for securing communications between an implantable wearable medical device (IWMD) and an external device (ED) is disclosed. The system includes a wireless radio frequency (RF) channel configured for communication between the IWMD and the ED. The system further includes a vibration-based side channel configured for verifying communication between
(Continued)

the IWMD and the ED such that the RF channel is activated only when the IWMD detects a vibration signal generated by an ED.

17 Claims, 7 Drawing Sheets

(51) Int. Cl.
*H04L 29/06* (2006.01)
*H04W 12/04* (2009.01)
*H04W 12/02* (2009.01)
*H04W 12/06* (2009.01)

(52) U.S. Cl.
CPC .............. *A61B 5/686* (2013.01); *H04L 63/18* (2013.01); *H04W 12/02* (2013.01); *H04W 12/04* (2013.01); *H04W 12/06* (2013.01); *A61B 5/002* (2013.01)

(56) References Cited

U.S. PATENT DOCUMENTS

| | | | |
|---|---|---|---|
| 6,580,947 | B1 | 6/2003 | Thompson |
| 6,985,773 | B2 | 1/2006 | Von Arx et al. |
| 7,155,290 | B2 | 12/2006 | Von Arx et al. |
| 8,024,043 | B2 | 9/2011 | Bange et al. |
| 8,345,879 | B2 | 1/2013 | Singh |
| 8,542,827 | B2 | 9/2013 | Razzell |
| 2003/0136418 | A1* | 7/2003 | Behm ................ G16H 40/67 128/899 |
| 2007/0032270 | A1 | 2/2007 | Orr |
| 2008/0071328 | A1* | 3/2008 | Haubrich ............ A61B 5/0031 607/60 |
| 2010/0261509 | A1 | 10/2010 | Kovvali et al. |
| 2014/0161273 | A1* | 6/2014 | Soufan ................ H04M 1/19 381/73.1 |
| 2014/0176317 | A1 | 6/2014 | Sawa et al. |
| 2014/0236077 | A1* | 8/2014 | Robertson ............ A61B 5/0006 604/66 |
| 2014/0300490 | A1 | 10/2014 | Kotz et al. |

OTHER PUBLICATIONS

Halevi, T et al. "On Pairing Constrained Wireless Devices Based on Secrecy of Auxiliary Channels: The Case of \coustic Eavesdropping" CCS' 10 conference, Chicago, Illinois, Oct. 4, 2010.*
WO 11/10071 Pearson (Polycom, INC).*
Saxena, N. et al. "Treat 'Em Like Other Devices: User Authentication of Multiple Personal RFID Tags", in Symposium on Usable Privacy and Security, poster session, Jul. 15-17, 2009.
Halevi, T et al. "On Pairing Constrained Wireless Devices Based on Secrecy of Auxiliary Channels: The Case of Acoustic Eavesdropping" CCS' 10 conference, Chicago, Illinois, Oct. 4, 2010.
International Search Report and Written Opinion for PCT/US16/17746 dated Apr. 29, 2016.
C. Zhan, W. B. Baine, A. Sedrakyan, and C. Steiner, "Cardiac device implantation in the United States from 1997 through 2004: A population-based analysis," Journal of General Internal Medicine, 2008.
J. Radcliffe, "Hacking medical devices for funand insulin: Breaking the human SCADA system," in Proc. Black Hat Conference, 2011.
D. Halperin, T. Heydt-Benjamin, B. Ransford, S. S. Clark, B. Defend, W. Morgan, K. Fu, T. Kohno, and W. H. Maisel, "Pacemakers and implantable cardiac defibrillators: Software radio attacks and zero-power defenses," in Proc. SSP, 2008.
C. Li, A. Raghunathan, and N. K. Jha, "Hijacking an insulin pump: Security attacks and defenses for a diabetes therapy system," in Proc. Health Com, 2011.
N. R. Potlapally, S. Ravi, A. Raghunathan, and N. K. Jha, "Analyzing the energy consumption of security protocols," in Proc. ISLPED, 2003.
P. C. Kocher, J. Jaffe, and B. Jun, "Differential power analysis," in Proc. CRYPTO, 1999.
N. Saxena, M. Uddin, J. Voris, and N. Asokan, "Vibrate-to-unlock: Mobile phone assisted user authentication to multiple personal RFID tags," in Proc. PerCom, 2011.
S. Lee, K. Fu, T. Kohno, B. Ransford, and W. H. Maisel, "Clinically significant magnetic interference of implanted cardiac devices by portable headphones," Heart Rhythm, vol. 6, No. 10, 2009.
T. Halevi and N. Saxena, "Acoustic eavesdropping attacks on constrained wireless device pairing," IEEE Trans. Inf. Forensics Security, vol. 8, No. 3, 2013.
S.-Y. Chang, Y.-C. Hu, H. Anderson, T. Fu, and E. Y. L. Huang, "Body area network security: Robust key establishment using human body channel," in Proc. HealthSec, 2012.
K. K. Venkatasubramanian, A. Banerjee, and S. K. S. Gupta, "EKG-based key agreement in body sensor networks," in Proc. InfoCom, 2008.
F. Xu, Z. Qin, C. C. Tan, B. Wang, and Q. Li, "IMDGuard: Securing implantable medical devices with the external wearable guardian," in Proc. InfoCom, 2011.—jamming potentially hostile wireless communication.
M. Rushanan, C. Swanson, D. F. Kune, and A. D. Rubin, "SoK: Security and privacy in implantable medical devices and body area networks," in Proc. SSP, 2014.
A. Hyvarinen and E. Oja, "Independent component analysis: Algorithms and applications," Neural Networks, vol. 13, No. 4-5, 2000.
I. Hwang, J. Cho, and S. Oh, "Privacy-aware communication for smartphones using vibration," in Proc. RTCSA, 2012.
D. Ford, "Cheney's defibrillator was modified to prevent hacking," CNN News, 2013.
N. Roy et al.: "Ripple: Communicating through Physical Vibration"; USENIX Association 12th USENIX Symposium on Networked Systems Design and Implementation (NSDI '15), May 4-6, 2015 • Oakland, CA, USA.

* cited by examiner

VIBRATION-BASED SECURE SIDE CHANNEL FOR MEDICAL DEVICES

CROSS-REFERENCE TO RELATED APPLICATIONS

This application claims priority to provisional applications 62/118,195 and 62/132,778, filed on Feb. 19, 2015 and Mar. 13, 2015 respectively, which are herein incorporated by reference.

GOVERNMENT RIGHTS IN THIS INVENTION

This invention was made with government support under Grants CNS-1219570, CNS-0953468, and CCF-1018358 awarded by the National Science Foundation. The government therefore has certain rights in the invention.

FIELD OF THE INVENTION

Embodiments of the present invention relate generally to medical devices, and more particularly, to a vibration-based secure side channel to safeguard wireless communication between medical devices and external devices.

BACKGROUND OF THE INVENTION

Implantable and wearable medical devices (IWMDs) are used for monitoring, diagnosis, and treatment of an ever-increasing range of medical conditions. Some non-limiting examples of IWMDs include deep brain neuro-stimulators, cochlear implants, pacemakers, gastric implants, and insulin pumps. IWMDs have become increasingly sophisticated over the years and are now commonly equipped with advanced features, such as wireless connectivity. Wireless connectivity can be used for health monitoring, device checkups, manual delivery of therapy, and reprogramming parameters. Healthcare professionals are able to remotely monitor a patient's health and device status through an external device (ED) without requiring the patient to visit their office. Patients may also use their own ED to monitor their health and device status. EDs include but are not limited to mobile devices such as mobile phones, smart phones, or tablet computers, or other processing devices such as personal computers or notebook computers.

While wireless connectivity in IWMDs enables convenient and timely access to medical data, hackers or other adversaries may take advantage of security vulnerabilities to obtain sensitive medical data from IWMDs or even take control of them.

Typically, radio frequency (RF) channels between two wireless devices are secured through the use of cryptographic techniques. Some examples include symmetric or asymmetric key cryptography. However, traditional cryptographic techniques are not directly applicable to IWMDs because IWMDs must be protected from unauthorized access without deterring or delaying the healthcare professionals' access to them, particularly when the patient requires immediate medical assistance. Typical security mechanisms do not address this tension, usually favoring the resistance to adversaries over the need for easy access in emergencies.

Securing a wireless channel between IWMDs and one or more EDs involves at least the following difficulties. First, only legitimate EDs should be able to activate an RF module in the IWMD and establish a wireless connection to it. If the RF module may be activated by any ED, adversaries may make repeated (possibly invalid) connection requests in order to deplete batteries in the IWMD. This is referred to as a battery drain attack. Second, for resource-constrained IWMDs, asymmetric cryptography is not suitable since it is significantly more expensive (in terms of computation and memory) than symmetric cryptography. Further, establishing a public-key infrastructure (PKI) is not practical due to its required cost and scope. Third, while symmetric cryptography may alleviate some of the computational costs, it requires a secure exchange of a shared secret key between two devices. Therefore, if symmetric cryptography is used, the encryption and decryption algorithms must be implemented efficiently to ensure immediate access from a healthcare professional if necessary.

Thus, there is a need for a secure wireless channel between IWMDs and EDs that enables quick access in the event of emergencies.

SUMMARY OF THE INVENTION

According to some embodiments, a system for securing communications between an implantable wearable medical device (IWMD) and an external device (ED) is disclosed. The system includes a wireless radio frequency (RF) channel configured for communication between the IWMD and the ED. The system further includes a vibration-based side channel configured for verifying communication between the IWMD and the ED such that the RF channel is activated only when the IWMD detects a vibration signal generated by an ED.

According to some embodiments, a method for securing radio frequency (RF) communication between an implantable wearable medical device (IWMD) and an external device (ED) is disclosed. The method includes the steps of periodically activating the IWMD to detect a vibration signal; placing the IWMD in a measurement mode if vibration is detected; high-pass filtering vibrations below a predetermined frequency while the IWMD is in the measurement mode; returning the IWMD to a standby mode if no vibration above the predetermined frequency is detected; and activating an RF channel for secure communication if vibration is detected above the predetermined frequency.

According to some embodiments, a non-transitory computer-readable medium having stored thereon a computer program for execution by a processor configured to perform a method of securing radio frequency (RF) communications between an implantable wearable medical device (IWMD) and an external device (ED) is disclosed. The method includes the steps of periodically activating the IWMD to determine if a vibration signal exceeds a predetermined threshold; placing the IWMD in a measurement mode if vibration is detected; high-pass filtering vibration below a predetermined frequency while the IWMD is in the measurement mode; returning the IWMD to a standby mode if no vibration above the predetermined frequency is detected; and activating an RF channel for secure communication if vibration is detected above the predetermined frequency.

Various other features and advantages will be made apparent from the following detailed description and the drawings.

BRIEF DESCRIPTION OF THE DRAWINGS

In order for the advantages of the invention to be readily understood, a more particular description of the invention briefly described above will be rendered by reference to specific embodiments that are illustrated in the appended drawings. Understanding that these drawings depict only exemplary embodiments of the invention and are not, therefore, to be considered to be limiting its scope, the invention will be described and explained with additional specificity and detail through the use of the accompanying drawings, in which.

DETAILED DESCRIPTION OF THE INVENTION

Disclosed herein is a vibration-based secure side channel, which can be used to safeguard a wireless connection between implantable and wearable medical devices (IWMDs) and external devices (EDs), particularly for the purpose of radio frequency (RF) module wakeup and cryptographic key exchange. Vibration is an intrinsically short-range, user-perceptible channel that is suitable for realizing physically secure communication at low energy and size/weight overheads. For instance, if the IWMD is implanted in the chest of a patient, a passive adversary (eavesdropper) cannot eavesdrop on the vibration channel without an eavesdropping device attached to the chest, which is highly likely to be noticed by the patient. Furthermore, since a vibration motor makes a highly perceptible vibration intended for user notifications, active attacks that inject vibration would be easily noticed by the patient as well. By waking up the RF module in the IWMD only upon detecting a vibration signal generated by a trusted ED, remote battery drain attacks on the wireless connection can be prevented. The ED is first trusted or authorized by the patient, allowing the ED to transmit a vibration. By being allowed to transmit vibration, it can then be trusted by the IWMD through receipt of the vibration. Since vibration can be received from an IWMD attached to the body, receipt of a vibration signal implicitly implies that the ED is trusted by the patient. If the ED cannot be trusted by the patient, it would be removed, and no vibration signal would be received by the IWMD.

Figure 1:
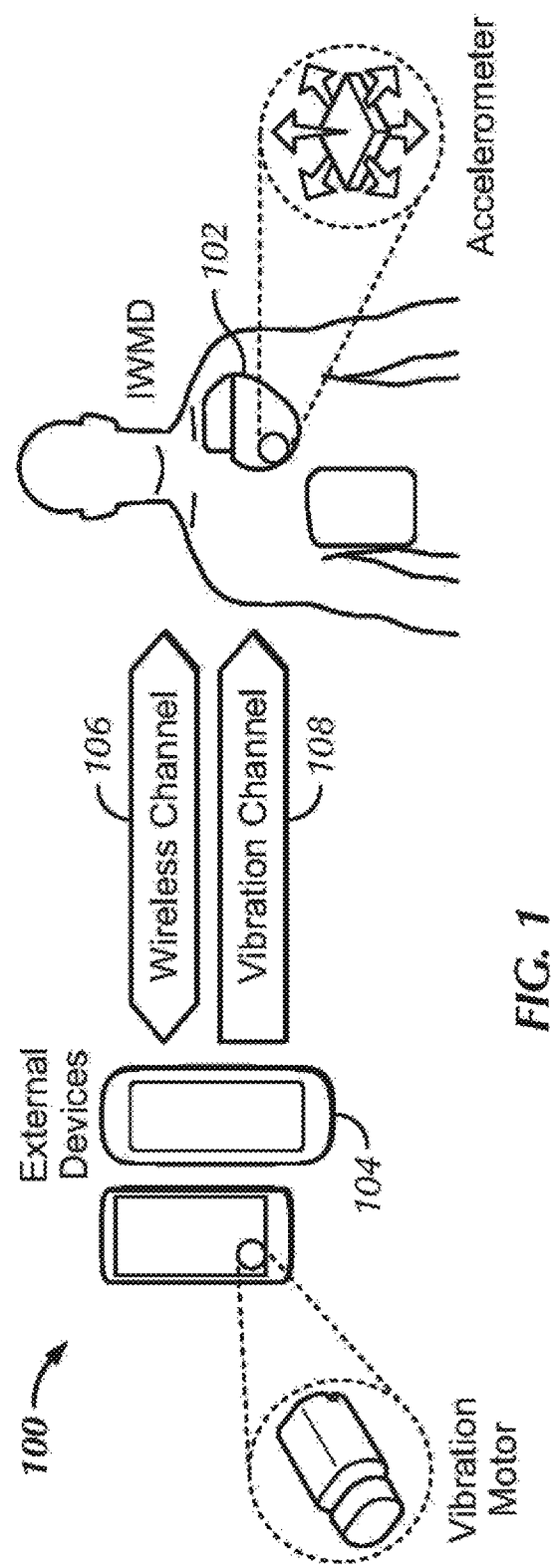
FIG. 1 is a diagram of a system for secure wireless communication between an implantable and wearable medical device and an external device in accordance with an embodiment of the invention.

FIG. 1 is a diagram of a system 100 for secure wireless communication between an IWMD 102 and an ED 104 in accordance with an embodiment of the invention. The IWMD 102 maybe a deep brain neuro-stimulator, a cochlear implant, a pacemaker, a gastric implant, or an insulin pump as non-limiting examples. The ED 104 may be a mobile device such as a mobile phone, smart phone, smart watch, or tablet computer, or other processing device such as a personal computer or notebook computer as non-limiting examples. The IWMD and ED communicate through a wireless RF channel 106 over a distance ranging from about 1 to 50 meters. The RF channel 106 designates ultra-high radio frequencies in the range between about 300 MHz and 3 GHz from transmitting and receiving information. IWMD 102 and ED 104 are capable of using symmetric encryption and cryptographic hashing for protecting information sent over the RF channel 106. To secure the communication through wireless channel 106 from hackers or other adversaries, system 100 includes a vibration side channel 108. The vibration channel 108 is a clean channel with little noise or interference. The frequency of vibration from a motor is typically higher than 150 Hz, which is not typically observed in ambient environment. Other sources of vibration, such as body motion or vehicle vibration, have much lower frequencies. Thus, a high-pass filter (not shown) can sufficiently eliminate all channel noise such that communication is not influenced by ambient vibrations.

Figure 2:
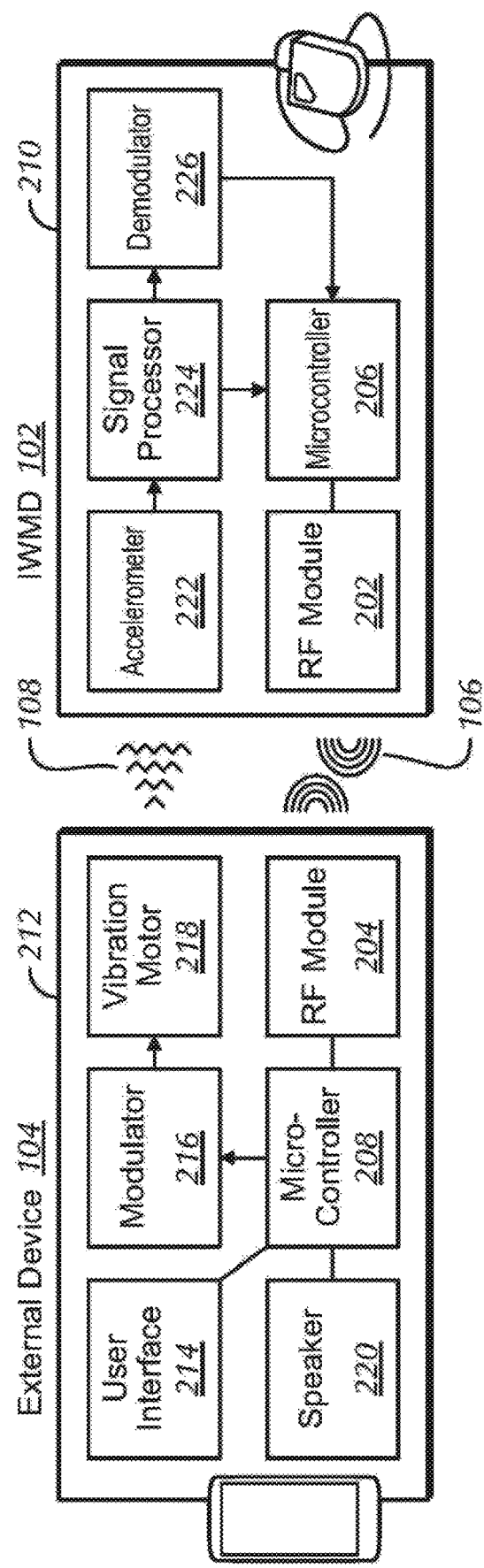
FIG. 2 is a block diagram of a system for secure wireless communication between an implantable and wearable medical device and an external device in accordance with an embodiment of the invention.

FIG. 2 is a block diagram of IWMD 102 and ED 104 in accordance with an embodiment of the invention. IWMD 102 and ED 104 each include a RF module 202 and 204, respectively, for wireless communication. Each RF module 202 and 204 includes a RF transceiver for both transmitting and receiving information. Such information may be used to remotely monitor a patient's health and/or implanted device. IWMD 102 and ED 104 each further include a microcontroller 206 and 208, respectively, for controlling the various components of IWMD 102 and ED 104. Each microcontroller 206 and 208 includes a processor for performing specific functions and memory for storing those functions. A system bus 210 and 212 is included in IWMD 102 and ED 104, respectively, for interconnecting the various components.

ED 104 further includes a user interface 214 for interaction with a patient or medical professional. User interface 214 includes a display component, input component, and navigation component. The display component may be a liquid crystal display (LCD) screen, an organic light emitting diode (OLED) screen, an active matrix OLED (AMOLED) screen, an LED screen, or a plasma display as non-limiting examples for displaying information to the patient or medical professional. The input component may be a keyboard or keypad as non-limiting examples for allowing a patient or medical professional to input information. The navigation component may be a mouse, trackball, or other such device for enabling a patient or medical professional to navigate along the display component. In some embodiments, display component, input component, and navigation component are implemented together in a touchscreen.

For transmitting vibration, ED 104 includes a modulator 216 and vibration source 218, such as a vibration motor. ED 104 further includes a speaker 220 for generating a masking sound.

IWMD 102 includes an accelerometer 222, a signal processor 224, and a demodulator 226 for receiving the vibration from ED 104. In some embodiments, the signal processor 224 and demodulator 226 can be incorporated as software in the microcontroller 206. The accelerometer 222 consumes low current (less than a few hundred µA in an active mode) and is small in size (only a few mm along any dimension). Such low energy overhead and small footprint are essential for prolonging the life of IWMD 102, since it leaves more room for a battery. To further decrease energy consumption, accelerometer can utilize a power management technique such as duty cycling. While IWMD 102 may include a second vibration source (not shown) for a bi-directional vibration channel, such inclusion is not practical due to energy costs and area overheads.

Figure 3:
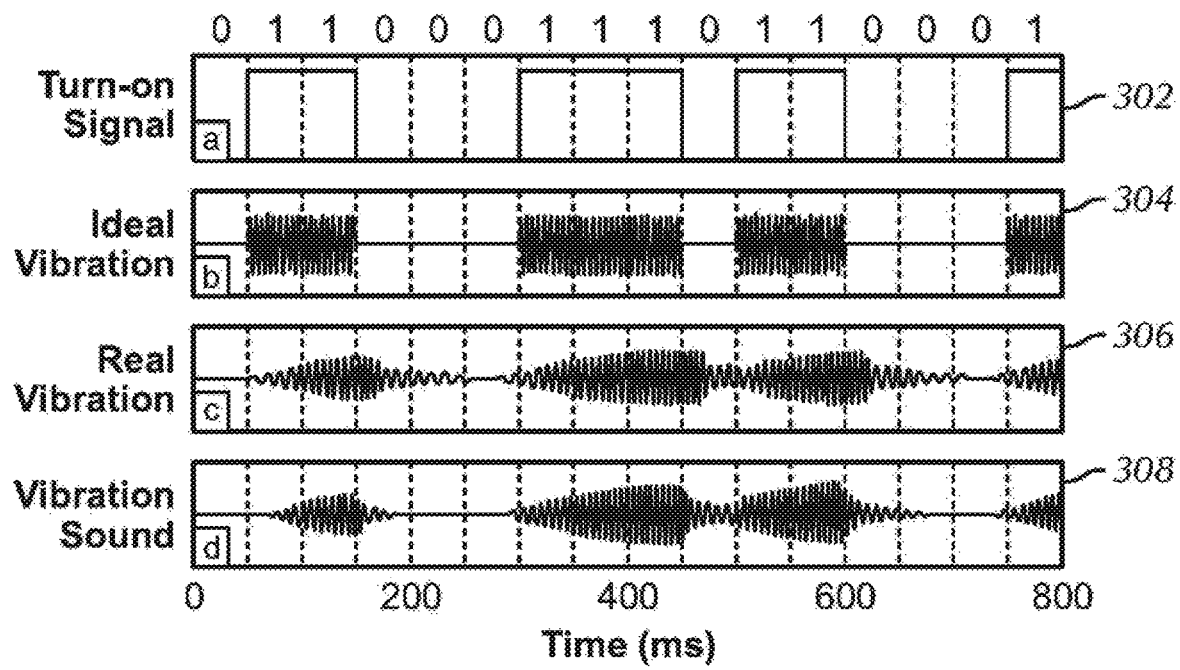
FIG. 3 is a graph of a vibration motor turn-on signal and corresponding ideal vibration, real measured vibration, and measured vibration sound in accordance with an embodiment of the invention.

One challenge of a vibration channel is that typical vibration motors exhibit a non-ideal, damped response to excitation. FIG. 3 illustrates a graph of a vibration motor turn-on signal and corresponding ideal vibration, real measured vibration, and measured vibration sound. For the signal 302, where a bit value of 1 turns a vibration motor on and a bit value of 0 turns it off, an ideally fast-responding motor would generate vibration as shown in signal 304. However, vibration of a real motor is not amplified or attenuated immediately, as shown by signal 306. With such a slow response, a simple on-off keying (OOK) scheme that maps bit 0 and bit 1 to zero amplitude and maximum amplitude, respectively, cannot achieve a bit rate of more than a few bits per second (bps). Further, a real vibration motor also leaks an audible acoustic signal, as shown by signal 308, which can be captured using a microphone for eavesdropping attacks.

To enable faster bit rates for key exchanges, an embodiment of the present invention incorporates a two-feature OOK scheme. Modulation (with modulator 216) utilizes an OOK scheme where the vibration motor is turned on to transmit a bit 1 and turned off to transmit a bit 0. Demodulation (with demodulator 226) of the vibration waveform is based on a combination of the amplitude gradient and amplitude mean of the waveform. Utilizing the amplitude gradient greatly enhances the distinction between bit 0 and bit 1 when the amplitude mean has an intermediate value, thereby enabling faster bit-rates (over 20 bps compared to 2-3 bps).

Figure 4:
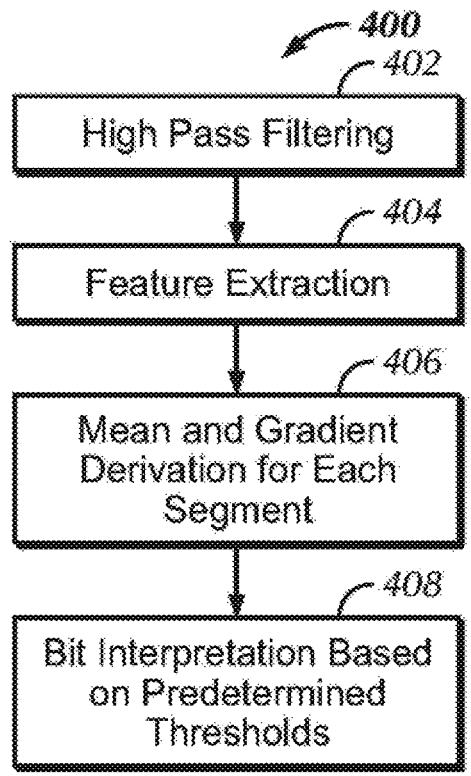
FIG. 4 is a flowchart of a demodulation process to enable faster bit rates in accordance with an embodiment of the invention.

FIG. 4 is a flowchart illustrating the demodulation process 400 to enable faster bit rates. At step 402, high-pass filtering is implemented to eliminate low frequency noise induced by patient movement or internal organs. In a preferred embodiment, a high-pass filter with a cutoff of 150 Hz is utilized, though in other embodiments, other cutoff ranges may be used so long as low frequency noise is eliminated. At step 404, feature extraction is implemented, where a signal envelope is derived and segmented into intervals equal to the bit period. At step 406, the amplitude mean and amplitude gradient for each segment are derived. At step 408, each bit is interpreted based on predetermined low and high thresholds. Steep negative gradients (lower than the low gradient threshold) and steep positive gradients (greater than the high gradient threshold) are interpreted as bit 0 and bit 1, respectively. Similarly, amplitudes below the low amplitude threshold and amplitudes above the high amplitude threshold are interpreted as a bit 0 and a bit 1, respectively. In an exemplary embodiment, the low/high gradient thresholds were about −2 g/s and +2 g/s respectively, and the low/high amplitudes thresholds were about 0.2 g and 0.4 g respectively, where g is the standard gravitational acceleration (9.8 m/s$^2$). Other embodiments may utilize other values based on the vibration motor used or pressure on the ED as nonlimiting examples. The ranges between the low and high thresholds represent classification margins. If at least one of the gradient and mean values lies outside the range between the corresponding low and high thresholds, the bit is labeled as a clear bit. When both the mean and gradient values lie between the corresponding low and high thresholds, the bit is labeled as an ambiguous bit, which is handled by a key exchange protocol to be discussed below.

Another critical challenge for vibration-based wakeup is reducing its energy consumption. Without proper power management, the energy consumed for continuous vibration measurement and signal processing for high-pass filtering may reduce the battery life of IWMDs. Typical IWMDs are expected to last about 90 months on a battery with 0.5 to 2 Ah capacity. Therefore, their average system-level current drain should not exceed 8 to 30 µA.

Figure 5:
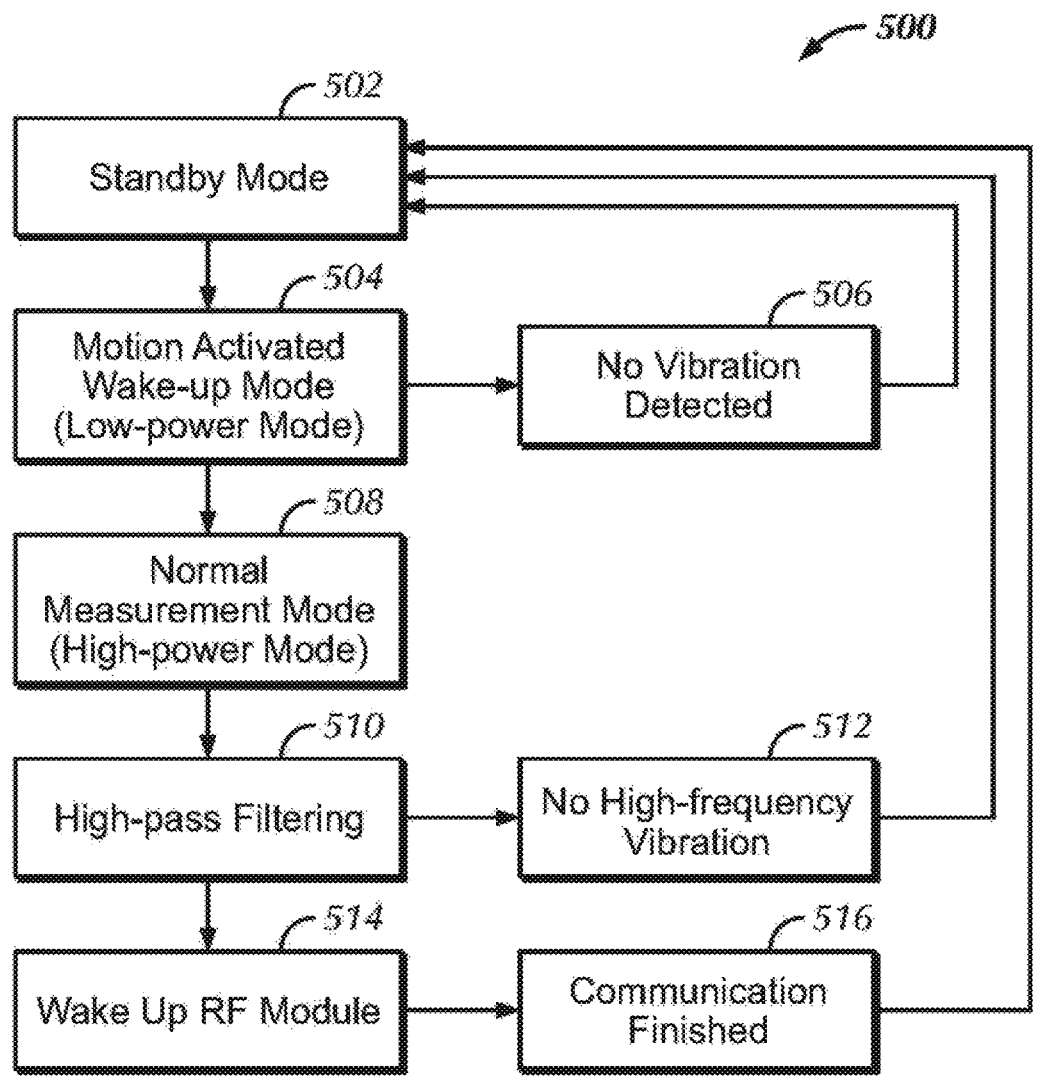
FIG. 5 is a flowchart of a two-step wakeup scheme for low power management in accordance with an embodiment of the invention.

To address this issue, an embodiment of the present invention includes a power management scheme such that the accelerometer 222 consumes lower power than a typical measurement mode. FIG. 5 is a flowchart illustrating a two-step wakeup scheme 500 for low power management. At step 502, the accelerometer 222 is in a standby mode such that minimal power is consumed. At step 504, the IWMD 102 periodically wakes up the accelerometer 222 and puts it into a motion-activated wakeup (MAW) mode for a short time to check if the vibration exceeds a specified threshold. The MAW mode lasts for just enough time to detect the existence of motor vibration, typically under 100 ms. The threshold can be set to slightly lower than the maximum amplitude of motor vibration, higher amplitude of which indicates the potential existence of motor vibration. Exemplary embodiments may use a threshold of ±0.5 g. The wakeup threshold is set to be able to detect the vibration generated by ED 104, but not to be activated by modest body motions. If no vibration is detected, accelerometer 222 returns to a standby mode at step 506. When vibration is detected, accelerometer 222 is placed in a measurement mode at step 508, where it measures the vibration at a full sampling rate. At step 510, the measured vibration is high-pass filtered to remove motion induced low-frequency vibration. If no high frequency vibration is detected, the accelerometer 222 returns to a standby mode at step 512. If high-frequency vibration is observed after filtering, the RF module 202 is turned on for communication at step 514. Once communication is complete, the accelerometer 222 returns to a standby mode at step 516. This power management scheme imposes less than 0.2% energy overhead for an energy budget of 1.5 Ah over 90 months.

Figure 6:
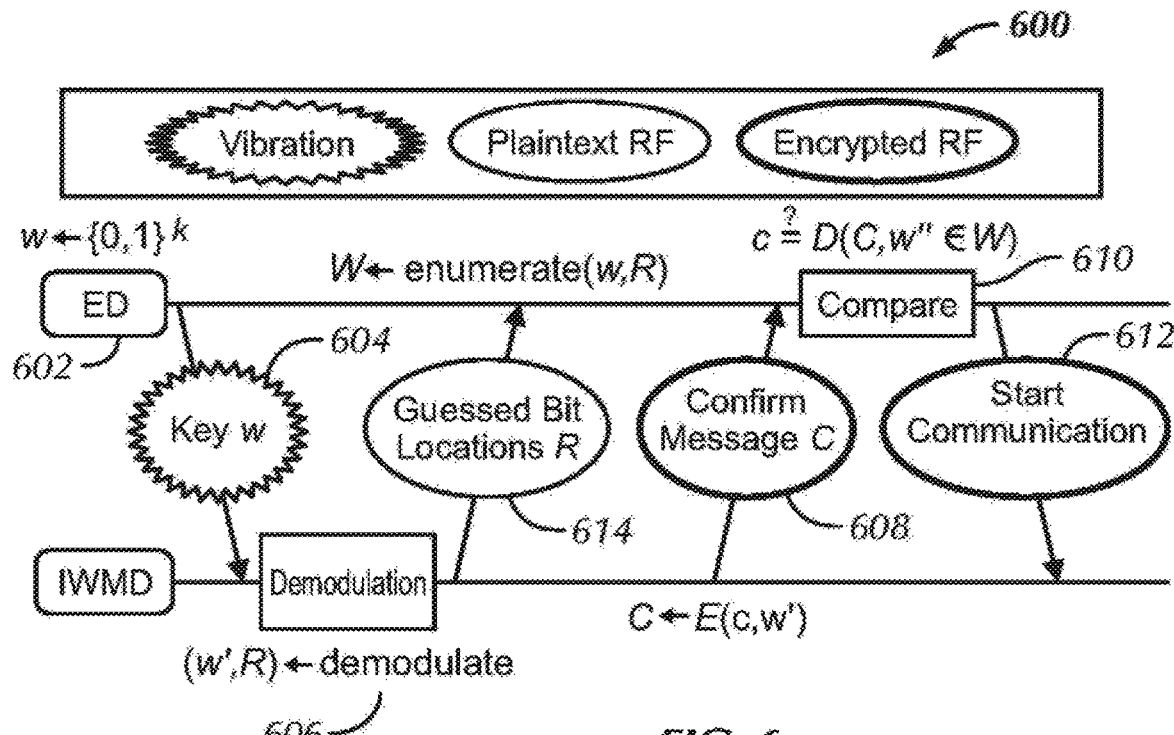
FIG. 6 is a chart of a key exchange protocol to make a medical device and an external device agree upon an identical key in the presence of errors introduced by a secure vibration channel in accordance with an embodiment of the invention.

After successful wakeup of the RF module 202 in the IWMD 102, a shared key needs to be exchanged between the IWMD 102 and ED 104 for the symmetric encryption of subsequent wireless communication. FIG. 6 is a chart illustrating a key exchange protocol 600 to make IWMD 102 and ED 104 agree upon an identical key in the presence of errors introduced by the vibration channel 108 according to an embodiment of the present invention.

At step 602, the ED 104 first generates a random key $w \in \{0,1\}^k = w_1 w_2 \ldots w_k$ of length k. At step 604, the key w is then modulated into vibration, which is received by the IWMD 102. At step 606, the key w is converted into a bit string w' using the two-feature OOK demodulation scheme described above with reference to FIG. 5. It is possible w' may differ from w due to errors during transmission. Therefore at step 608, IWMD 102 encrypts a predefined, fixed confirmation message c using w' as the key to get a ciphertext C=E(c, w') and transmits it to the ED 104 through the RF channel 106. If C is successfully decrypted by the ED 104 with w, i.e., if D(E(c, w'),w)=c at step 610, the ED 104 knows that the IWMD 102 received the key w correctly. Subsequent wireless communication is then encrypted using the key w at step 612.

The received vibration signal may contain ambiguous bits, which are when both mean and gradient values lie between corresponding low and high thresholds, discussed above with regards to the demodulation process. The ambiguous bits may lead to bit error after demodulation since w'≠w and repeating the entire key exchange process until the IWMD 102 receives w correctly may take too much time and energy. Therefore, when the number of ambiguous bits is small, a key reconciliation step is performed instead of re-starting the entire key exchange process because the IWMD 102 and ED 104 only need to agree upon a random key, which is not restricted to the original key w.

For key reconciliation, shown by step 614, the IWMD 102 makes random guesses for the values of the ambiguous bits to create w' and sends only the locations of those bits, R, to the ED 104 using the RF channel 106. The IWMD 102 also encrypts the fixed message c into C with w' and sends it to the ED 104. The ED 104 performs an exhaustive enumeration of all possible values for the bits in R, and obtains a set of key candidates W. If any key w"∈W can decrypt C, the key exchange is successful.

As an example of the key reconciliation process, consider a case in which k=4 and w=1011. Assume that $w_2$ and $w_3$ are ambiguous, and the IWMD 102 makes guesses that $w_2$=1 and $w_3$=0, resulting in w'=1101 and R={2,3}. Upon receiving R, the ED 104 prepares a set of candidate keys W={1001, 1011, 1101, 1111}. Since C can be decrypted by one of these keys, i.e., 1101, the IWMD 102 and ED 104 can start encrypted communication with this key.

If the number of ambiguous bits detected during demodulation exceeds a predefined limit, or if none of w"∈W is able to decrypt C, the key exchange process is restarted with a fresh random key.

The present key exchange protocol minimizes the effort expended by the IWMD 102 for key reconciliation. The IWMD 102 prepares only one key w', encrypts c with it, and sends C only once. The IWMD 102 is not burdened with any extraneous computation or communication compared to prior embodiments where w' must exactly match w. Instead, the ED 104 is required to perform multiple decryption trials using the various candidate keys, but the ED 104 has a larger energy budget and computational power than the IWMD 102.

Possible attacks from hackers or other adversaries can occur on the vibration channel 108 or RF channel 106; however, embodiments of the present invention may employ one or more countermeasures against them to ensure security between the IWMD 102 and ED 104. Attacks on the vibration channel 108 include passive attacks to eavesdrop on the key exchange using an accelerometer and active attacks to illegitimately wake up the RF module 202 using a vibration motor. However, due to the short transmission range, active attacks on the vibration channel 108 are likely not possible.

More likely, attacks on the vibration channel 108 will be passive acoustic eavesdropping, which captures the sound generated by the vibration motor 218 and uses suitable signal processing techniques to recover the encryption key. Sophisticated forms of this attack may use multiple microphones and differential analysis to mitigate noise. However, embodiments of the present invention implement an acoustic masking as a countermeasure utilizing a speaker 220 on the ED 104. When the ED 104 transmits the key through the vibration channel 108, the ED 104 also generates a masking sound pattern from its speaker 220. To maximize the effectiveness of masking, a band-limited Gaussian white noise restricted to the same frequency range as the acoustic signature of the vibration motor 218 may be utilized. This also makes the masking sound less unpleasant to the user.

Another passive attack is to eavesdrop directly on the RF channel 106. If a hacker or other adversary eavesdrops on the RF channel 106 during the key exchange process, he or she may obtain locations of the guessed bits, R, and the encrypted confirmation message C. From R, the hacker or adversary can determine which bits of the key are randomly guessed by the IWMD 102. However, this information about the locations of random bits does not provide any information about the actual values of those bits. The key reconciliation is equivalent to generating a key by combining k−|R| random bits from the ED 104 and |R| random bits from the IWMD 102. Further, since c is encrypted only once by the IWMD 102 and only a single C is sent to the ED 104, other related-key attacks are not feasible.

A prototype embodiment of the present invention was developed to evaluate the vibration based secured side channel against possible attacks. In this prototype embodiment, the IWMD platform was based on the nRF51822 RF system-on-chip (SoC), which has an ARM Cortex M0 core and a 2.4 GHz transceiver for Bluetooth Smart, and supports two different accelerometers with distinct power and sampling rate specifications. The ADXL362 accelerometer consumes low power (3 µA in an active mode, 270 nA in a MAW mode, and 10 nA in a standby mode), which is suitable for persistent motion detection, but its sampling rate is limited to 400 sps. The ADXL344 accelerometer has a higher sampling rate of up to 3200 sps, but due to its high power consumption (140 µA in active mode), it is more suitable for an occasional higher sampling rate measurement. A Google Nexus 5 smartphone was used as the ED platform. An Android application that generates a random cryptographic key was developed that executes the proposed wakeup scheme and key exchange protocol (while concurrently playing a masking sound) according to an embodiment of the present invention. The human body was emulated using a model comprising a 1-cm layer of bacon on a 4-cm layer of ground beef. The IWMD platform was placed between the bacon and ground beef, which reflects a typical implantation of an implantable cardioverter defibrillator. The ED platform is placed directly on the bacon layer with a thin plastic sealing.

Figure 7:
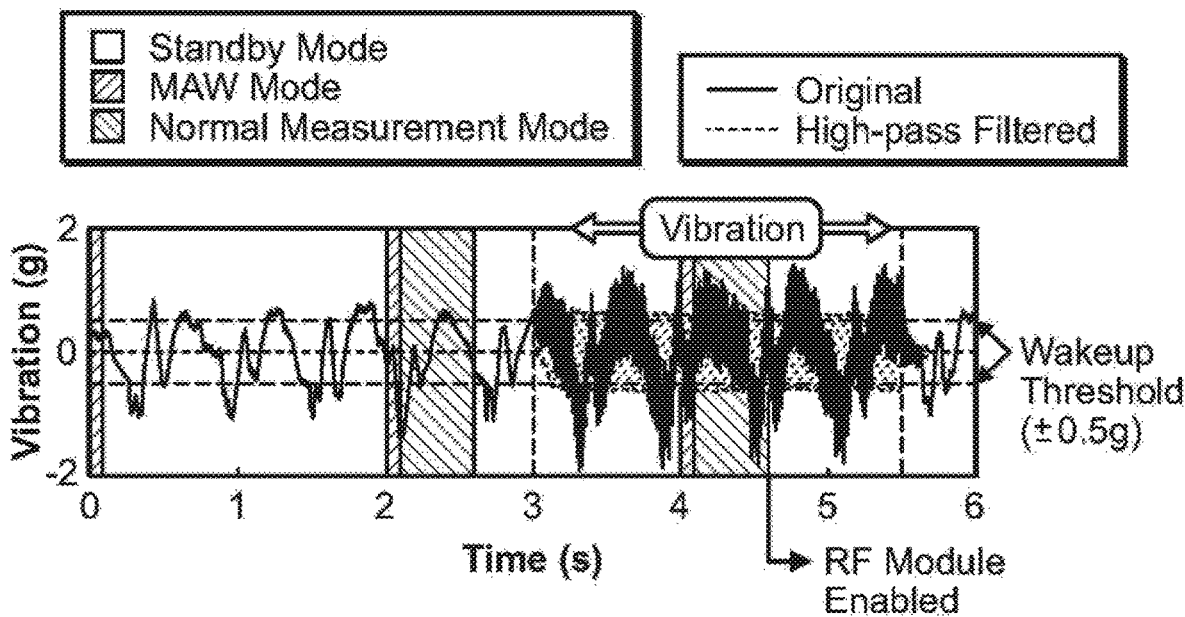
FIG. 7 is a graph of experimental results of the vibration based wakeup scheme in accordance with an embodiment of the invention.

First, the vibration based wakeup scheme was demonstrated with the ADXL362 accelerometer to estimate its power consumption. The scheme was evaluated in the presence of motion-induced noise by having a person walk with the prototype embodiment. The experimental results are shown in FIG. 7. The period of duration of the MAW mode are 2 s and 100 ms, respectively, and the duration of the normal measurement mode is 500 ms. FIG. 7 shows the original vibration signal and the high-pass filtered vibration with a passband of 150 Hz. The accelerometer did not detect any significant vibration in the first MAW period, and hence returned to the standby mode immediately. In the next MAW period, the large vibration due to the motion of walking made the accelerometer enter the normal measurement mode for 500 ms for full-rate sampling. However, as no vibration was detected after high-pass filtering, it returned to the standby mode without enabling the RF module. In the third MAW period, the accelerometer again entered the normal measurement mode. This time, the residual vibration after high-pass filtering is accepted as a wakeup signal, and the RF module is enabled. For these settings, the slowest wake up time is 2.5 s: 1.8 s in the standby mode, 200 ms in the MAW mode, and 500 ms in the normal measurement mode. Wakeup time can be traded off against energy consumption by varying the time spent in the standby mode. For instance, if MAW mode is entered once every 10 s and the false-positive vibration detection rate is 20%, the average current consumption of the accelerometer is about 43 nA. For an IWMD with a 1.5 Ah battery and 90 month lifetime, this corresponds to less than 0.2% of the power budget of the IWMD.

Figure 8:
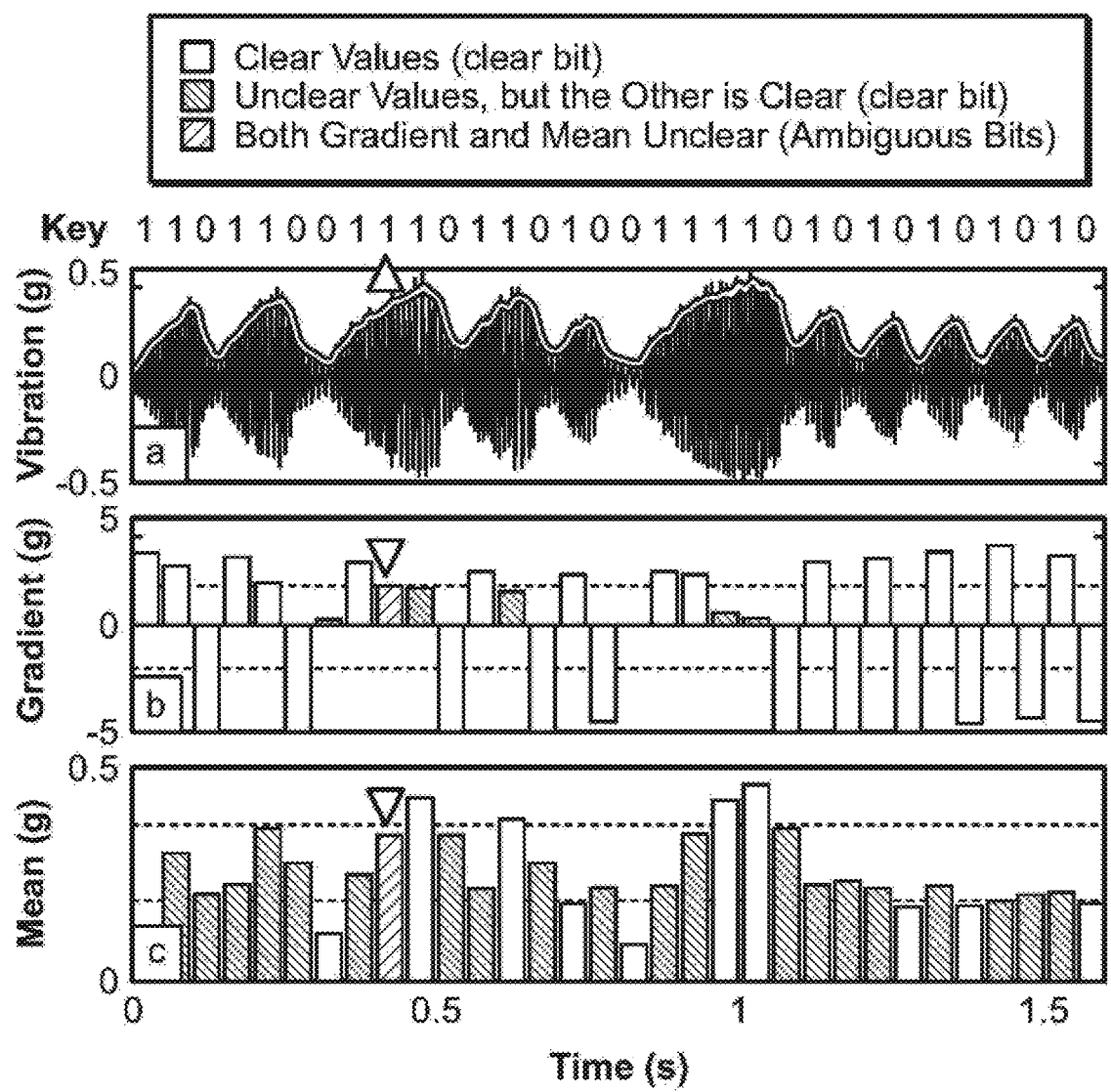
FIG. 8 is a graph of a measured waveform for an experiment key exchange in accordance with an embodiment of the invention.

Second, the cryptographic key exchange was demonstrated using the prototype embodiment with the bit rate set to 20 bps. This bit rate enables the exchange of a 256-bit key in 12.8 s. A measured waveform for a 32-bit key exchange is shown in FIG. 8. In FIG. 8($a$), the bit string at the top is modulated into vibration measured by the IWMD platform, and the curve represents its envelope. FIGS. 8($b$) and 8($c$) display the amplitude gradient and amplitude mean of each segment respectively. The dashed lines denote the high and low thresholds. Out of 32 bits, 31 bits may be demodulated clearly, but the $9^{th}$ bit, which is highlighted with a triangular mark, was an ambiguous bit. Therefore, the ED platform receives R={9} from the IWMD platform, and may find w' within two trials to decrypt C.

Figure 9:
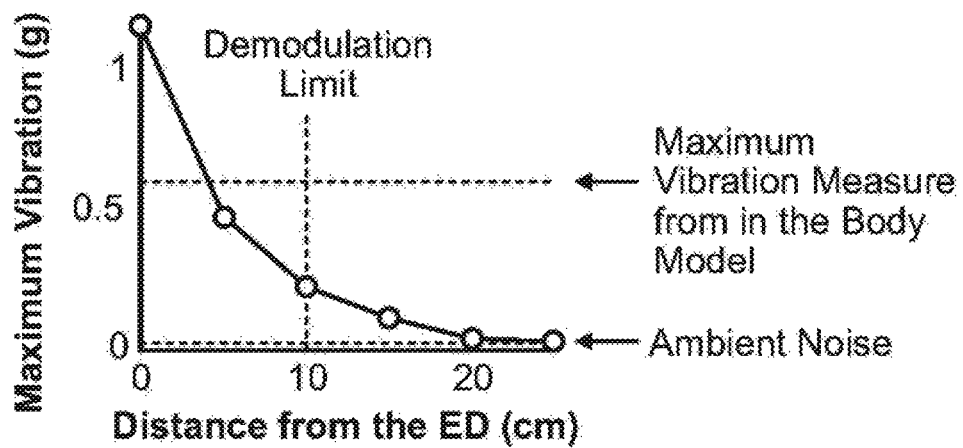
FIG. 9 is a graph of vibration amplitude measured at distances from a vibrating external device in accordance with an embodiment of the invention.

Third, various security attacks on the vibration channel were evaluated. In order to determine the feasible range of direct attacks on the vibration channel, the ED platform was placed on the chest of a human subject, the vibration at the body surface was measured at varying distances from the ED platform, and the cryptographic key was attempted to be recovered. FIG. 9 shows the vibration amplitude measured at distances of 0 to 25 cm from the vibrating ED platform. The vibration exponentially attenuates with distance and the key exchange was successful only within 10 cm. Therefore, in order to pick up the vibration, an eavesdropping device should be placed on the body surface within 10 cm of the IWMD platform, which is not likely possible. At 25 cm, the vibration is no more than the ambient noise, filtered out by the high pass filter.

Figure 10:
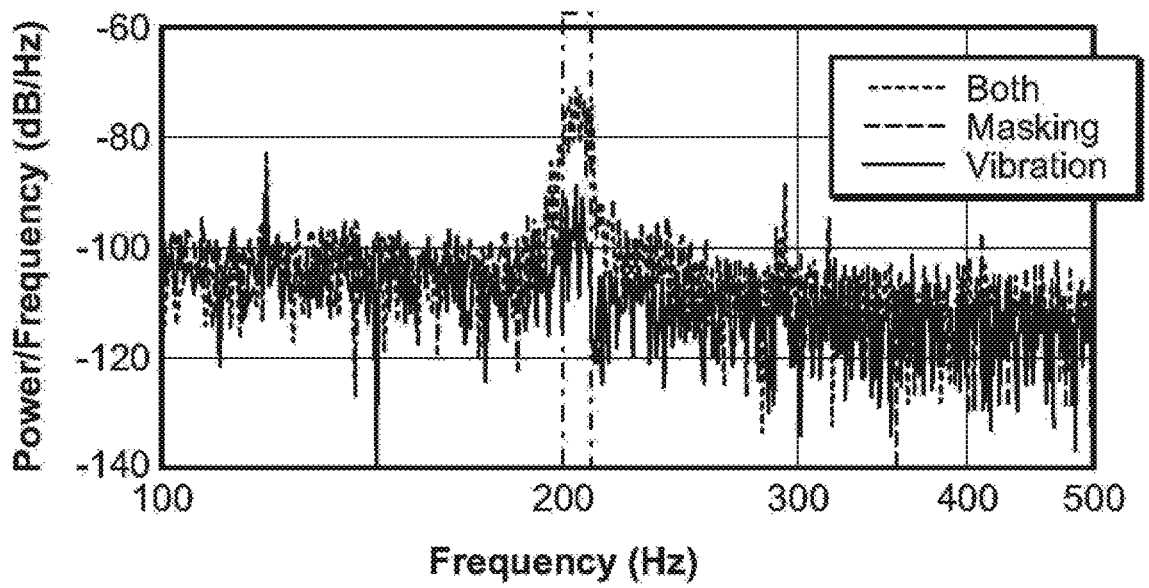
FIG. 10 is a graph of a power spectral density comparison of three sounds: vibration sound only, masking sound only, and vibration sound with masking sound in accordance with an embodiment of the invention.

The potential of acoustic eavesdropping attacks were also evaluated. The vibration sound and masking sound were measured 30 cm away from the ED platform in an attempt to obtain the cryptographic key from the recorded sound waveform instead of the vibration waveform measured by the accelerometer. It was assumed that the hacker also has access to the RF channel and is able to know from R which bits are guessed by the IWMD platform and is able to accurately find the beginning of the vibration. Even after making such assumptions, the vibration may not be successfully demodulated into the correct key due to the strong masking sound. FIG. 10 shows a power spectral density comparison of three sounds: vibration sound only, masking sound only, and vibration sound with masking sound. These measurements were taken in a room with an ambient noise level of 40 dB. The vibration sound is significant in the frequency range of 200 to 210 Hz, and the masking sound is stronger than the vibration sound in this range by at least 15 dB, thus explaining the effectiveness of the masking scheme.

A hacker may be capable of performing differential attack by recording sound at multiple locations. Independent component analysis (ICA) technique separates a signal into additive subcomponents and can be used to separate two sound sources measured from two different locations. Since the vibration sound and masking sound are generated from different sources (vibration motor and speaker, respectively), the attacker may try to separate the vibration sound using ICA techniques. To evaluate the effectiveness of a differential attack, two identical microphones were placed each at a distance of 1 m (a reasonable distance for acoustic eavesdropping), but on opposite sides of the ED platform. The microphones were used to eavesdrop on a key exchange in the presence of acoustic masking. Running a FastICA algorithm produced two waveforms, one of which is expected to be the vibration sound, and the other one to be the masking sound. However, neither of the two separated waveforms may be demodulated successfully because the two sound sources are too close to each other in frequency for the channel difference to be recognized by the two microphones.

Thus, disclosed herein is a secure side channel based on vibration for enabling secure wireless communication with IWMDs. Vibration has unique advantages for realizing a secure side channel, such as close proximity requirements, user perceptibility, and low power consumption. Based on the vibration channel, disclosed herein is a low-power wakeup scheme for IWMDs to prevent battery drain attacks and a key exchange scheme for sharing a secret key used for subsequent protection of the RF channel between the IWMD and ED. To enable acceptable key exchange times, disclosed herein is a two-feature OOK to increase the bit rate achievable using the vibration channel.

It is understood that the above-described embodiments are only illustrative of the application of the principles of the present invention. The present invention may be embodied in other specific forms without departing from its spirit or essential characteristics. All changes which come within the meaning and range of equivalency of the claims are to be embraced within their scope. Thus, while the present invention has been fully described above with particularity and detail in connection with what is presently deemed to be the most practical and preferred embodiment of the invention, it will be apparent to those of ordinary skill in the art that numerous modifications may be made without departing from the principles and concepts of the invention as set forth in the claims.

What is claimed is:

1. A system for securing communications between an implantable or wearable medical device (IWMD) and an external device (ED), the system comprising:
   a wireless radio frequency (RF) channel configured to communicate medical information between the IWMD and the ED; and
   a vibration-based side channel configured to verify the communication of medical information between the IWMD and the ED;
   the RF channel being activated when the IWMD detects a vibration signal generated by the ED via a motion sensing device of the IWMD and determines an amplitude gradient and amplitude mean of the vibration signal are above respective thresholds via a demodulator of the IWMD.

2. The system of claim 1, wherein the IWMD comprises a high-pass filter to eliminate vibration channel noise.

3. The system of claim 1, wherein the IWMD and ED each comprise a RF module configured to transmit, receive, or transmit and receive the medical information.

4. The system of claim 1, wherein the ED is a mobile device.

5. The system of claim 1, wherein the ED comprises a modulator and vibration source for transmitting the vibration signal.

6. The system of claim 1, wherein the ED comprises a speaker configured to generate a masking sound to mask the vibration signal.

7. The system of claim 1, wherein the motion sensing device comprises an accelerometer.

8. The system of claim 1, wherein an encryption key is transmitted through the vibration channel to the IWMD.

9. The system of claim 8, wherein the medical information is encrypted when the IWMD receives the encryption key.

10. The system of claim 9, wherein the IWMD performs a key reconciliation process when the encryption key includes one or more ambiguous bits.

11. A method for securing radio frequency (RF) communication of medical information between an implantable or wearable medical device (IWMD) and an external device (ED) via a vibration-based side channel, the method comprising the steps of:
- activating the IWMD to detect a vibration signal;
- placing the IWMD in a measurement mode when a vibration signal is detected;
- high-pass filtering vibration signals below a predetermined frequency when the IWMD is in the measurement mode, the IWMD to return to a standby mode when no vibration signals above the predetermined frequency are detected; and
- activating an RF channel for secure communication of the medical information when a vibration signal detected above the predetermined frequency has an amplitude gradient and amplitude mean above respective thresholds.

12. The method of claim 11, further comprising receiving a vibration signal from an ED.

13. The method of claim 11, further comprising masking the vibration signal.

14. The method of claim 11, further comprising transmitting an encryption key through the vibration-based side channel.

15. The method of claim 14, further comprising encrypting the medical information when the IWMD receives the transmitted encryption key.

16. The method of claim 15, further comprising performing a key reconciliation process when the transmitted encryption key includes one or more ambiguous bits.

17. A non-transitory computer-readable medium having stored thereon a computer program for execution by a processor configured to perform a method of securing radio frequency (RF) communications between an implantable or wearable medical device (IWMD) and an external device (ED) via a vibration-based side channel, the method comprising:
- activating the IWMD to detect a vibration signal;
- placing the IWMD in a measurement mode when a vibration signal is detected;
- high-pass filtering vibration signals below a predetermined frequency when the IWMD is in the measurement mode, the IWMD to return to a standby mode when no vibration signals above the predetermined frequency are detected; and
- activating an RF channel for secure communication when a vibration signal detected above the predetermined frequency has an amplitude gradient and amplitude mean above respective thresholds.

* * * * *